United States Patent [19]
Campbell, Jr. et

[11] 3,995,968
[45] Dec. 7, 1976

[54] TURBINE ROTOR DISC HAVING ULTRASONIC INSPECTION SURFACE THEREON

[75] Inventors: George T. Campbell, Jr., Swarthmore; Thomas P. Sherlock, Lansdowne, both of Pa.

[73] Assignee: Westinghouse Electric Corporation, Pittsburgh, Pa.

[22] Filed: Dec. 24, 1974

[21] Appl. No.: 536,069

[52] U.S. Cl. ................................. 403/356; 403/27; 73/71.5 US; 403/11
[51] Int. Cl.² ...................... F16D 1/08; G01N 23/02
[58] Field of Search ............ 403/356, 357, 358, 11, 403/27; 416/61; 73/67.3 R, 71.5 US

[56] References Cited
UNITED STATES PATENTS

| | | | |
|---|---|---|---|
| 1,107,238 | 8/1914 | Kieser | 403/356 X |
| 1,734,188 | 11/1929 | Wilson | 403/356 |
| 1,873,956 | 8/1932 | Dahlstrand | 403/358 |
| 3,513,802 | 5/1970 | Potter | 403/358 X |

*Primary Examiner*—Andrew V. Kundrat
*Attorney, Agent, or Firm*—G. H. Telfer

[57] ABSTRACT

A rotor disc for a rotor shaft member of an axial flow turbine apparatus is disclosed. The disc has disposed externally thereon a flat surface which lies parallel to a predetermined longitudinal plane extending within the disc. The plane is disposed within the disc so as to extend through a keyway utilized to prevent rotation of the disc relative to the shaft. The predetermined longitudinal plane within the disc is the plane in which cracking of the disc is most likely to occur. The externally disposed, flat, surface area of the disc permits an ultrasonic signal emitted from a transducer disposed adjacent to the external surface to propagate in a direction substantially perpendicular to the predetermined plane within the disc.

3 Claims, 3 Drawing Figures

U.S. Patent     Dec. 7, 1976     3,995,968
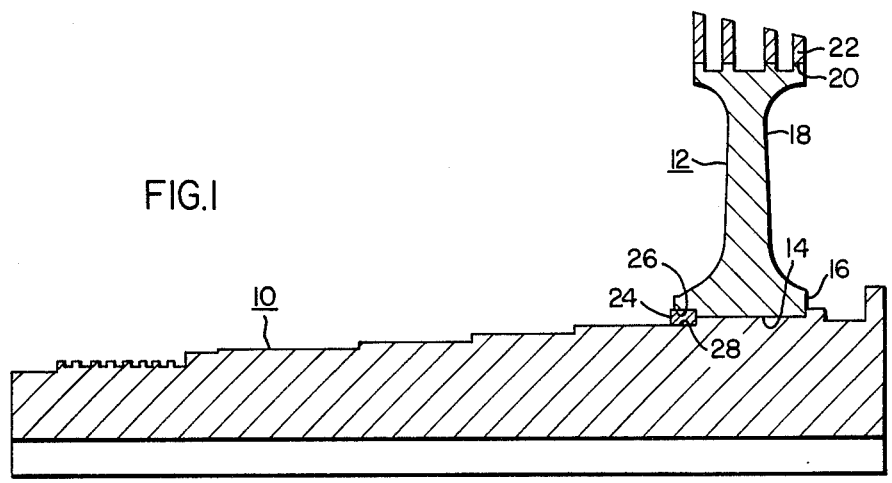
FIG.1
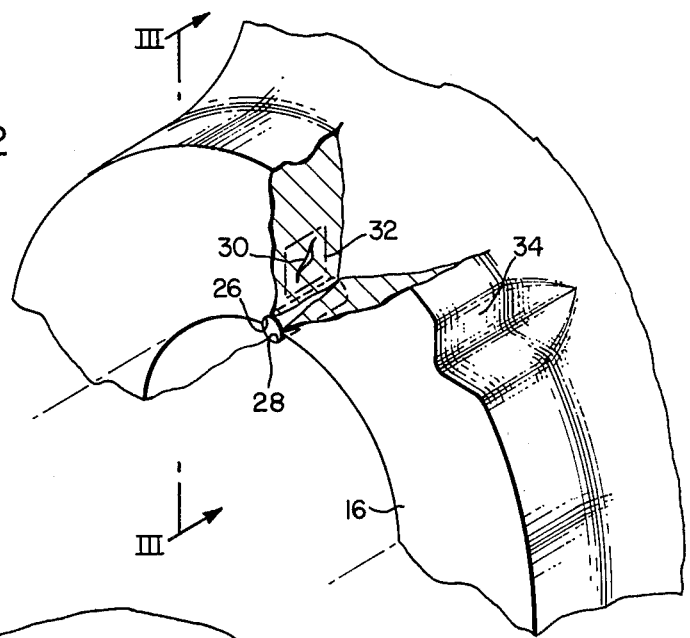
FIG.2
FIG.3

TURBINE ROTOR DISC HAVING ULTRASONIC INSPECTION SURFACE THEREON

BACKGROUND OF THE INVENTION

1. Field of the Invention

This invention relates to turbine apparatus and, in particular, to rotor discs having a surface thereon to facilitate detection of internal material faults occurring within the disc.

2. Description of the Prior Art

An axial flow elastic fluid turbine apparatus has rotatably disposed therein a rotor member which carries a plurality of arrays of rotating blades. The rotating blades interact with motive fluid directed thereon by stationary blades disposed within a cylindrical casing to transform the energy carried by the motive fluid into rotational mechanical energy. The rotating blades may be mounted onto the shaft portion of the rotor by insertion of a serrated root on each blade into a correspondingly shaped groove disposed on the periphery of the shaft. However, in very large, low pressure turbines, it is common practice to dispose the rotating blades in grooves fabricated on the periphery of a disc member which has been shrunk fit on to the shaft. The disc is a substantially annular shaped member forged from suitable material which, when heated to a predetermined temperature, expands so that it may be placed on the segment of the shaft which has a diameter larger than the disc bore. As the disc cools, it is firmly secured to the shaft. The disc is then said to have been shrunk fit to the shaft. One or more arrays of rotating blades may be received by each disc. In order to prevent rotation of the disc relative to the shaft, a key member is inserted into a keyway defined by aligned channels in the disc and the shaft. In prior art, both rectangular and cylindrical keys have been utilized for this purpose.

The discs, however, have been known to fracture due to stresses imposed thereon by the operation of the turbine apparatus. Fracturing of the disc can damage not only the turbine in which it is mounted, but also adjacent units, and may require shutdown of an entire power generating facility. One of the most notable happenings of this sort occurred at Hinkley Point Power Station in England in 1969. The catastrophic failure of a turbine within the Hinkley Point Station is documented and discussed in depth in articles by D. Kalderon and J. L. Gray, submitted to the Institution of Mechanical Engineers. The Kalderon paper is found in the Proceedings of the Institution of Mechanical Engineers, Volume 186, No. 31/72, while Gray's paper appears in Volume 186, No. 32172.

Kalderon concludes that the cause of the disc burst at the Hinkley Point centered upon stress-corrosion cracking of a semicircular keyway machined into the bore of the rotor disc. The cracking was demonstrated to have occured in a plane within the disc extending longitudinally through the keyway.

It is apparent that it is of great importance to be able to determine whether stresses imposed by operation of the turbine apparatus on the disc result in the formation and propagation of cracks within the disc. Of course, visual inspection of the keyway of the fabricated rotor disc-shaft arrangement is not possible. However, as is pointed out in a comment to the above cited articles of Kalderon and Gray, found at page D121–122 of the Proceedings of the Institution of Mechanical Engineers, a two-probe ultrasonic technique has been developed and used in the prior art. The author of the comment also mentioned the fact that a single probe technique has been developed for ultrasonic interrogation for disc geometries incompatible with the two-probe technique.

SUMMARY OF THE INVENTION

This invention relates to a rotor disc having a flat, machined, external surface area thereon, the external surface area being substantially parallel to a predetermined longitudinal plane extending through a keyway within the disc. The predetermined longitudinal plane is the plane in which cracking of the disc is most expected to occur. The external surface area is disposed such that an ultrasonic probe acoustically coupled thereagainst emits an interrogation signal that is substantially perpendicular to the expected plane of cracking.

It is an object of this invention to facilitate ultrasonic inspection of turbine rotor discs keyed onto a shaft member in an axial flow turbine apparatus. It is a further object to provide a surface area on the external surface of the rotor disc which permits expeditious, on-site, ultrasonic interrogation of the disc. Other objects of the invention will be made clear in the discussion of the preferred embodiment which follows herein.

BRIEF DESCRIPTION OF THE DRAWINGS

The invention will be more fully understood from the following detailed description taken in conjunction with the accompanying drawings, in which:

FIG. 1 is an elevational view entirely in section, of a rotor member for an axial flow turbine apparatus;

FIG. 2 is a perspective view of a rotor disc having an external surface disposed thereon according to the teachings of this invention; and, FIG. 3 is a view of a rotor disc embodying the teachings of this invention taken along line III—III of FIG. 2.

DESCRIPTION OF THE PREFERRED EMBODIMENT

Throughout the following description, similar reference numerals shall refer to similar elements in all figures of the drawings.

Referring first to FIG. 1, an elevational view entirely in section, of a portion of a rotor member 10 for an axial flow turbine apparatus embodying the teachings of this invention is shown. The rotor 10 is a substantially cylindrical member, having at least one annular disc member 12 shrunk fit thereon. The disc 12 is an annular member having a central bore 14 and is forged from suitable material, such as low alloy steel. The disc 12 has a hub portion 16 and a web, or steeple, portion 18 integral therewith. As seen in FIG. 1, the web 18 has a greater outside diameter than the outside diameter of the hub. A plurality of axial grooves 20 are disposed about the periphery circumferential of the web portion 18 and each groove 20 receives a root portion of a corresponding plurality of rotating blades 22. Although FIG. 1 shows four arrays of rotating blades 22 disposed on the disc 12, it is understood that any number of rotating arrays of blades may be carried on an individual disc member. The entire fabricated rotor is inserted into a stationary cylinder (not shown) having a plurality of arrays of stationary nozzle blades therein. The stationary nozzle blades direct an axial flow of motive fluid onto the alternating rows of rotating blades to convert the temperature and pressure energy of the motive fluid into rotational mechanical energy.

The disc 12 is shrunk fit onto the shaft 10 by heating the disc to a predetermined temperature and permitting it to expand. The disc 12 is then placed on the shaft 10 and allowed to cool and contract. In order to prevent rotation of the disc 12 relative to the shaft 10, a cylindrical key 24 is inserted into a keyway defined by aligned channels 26 and 28 machined into the hub portion 14 of the disc 12 and the shaft 10, respectively. It is the usual practice in the art to machine the keyway after the disc 12 has been placed on the shaft 10. The key 24 may extend under the entire axial dimension of the disc 12, or, as is the practice, extend only a predetermined axial distance therebetween. Commonly, the key 24 is a cylindrical member and extends axially between the disc 12 and the shaft 10 for a distance of 4 inches.

Once disposed upon the rotor shaft 10, and placed in a completed turbine apparatus, stresses are imposed upon the rotor disc 12 due to the operation of the turbine. Such stresses have been, on occasion, severe enough to cause fracture and bursting of the disc. Such an occurrence has happened at the Hinkley Point Power Station and which caused damage not only to the turbine, whose disc had burst, but to adjacent apparatus as well. It is apparent then, that it is desirable to be able to determine whether stresses imposed upon the disc members of a turbine by the operating conditions within the turbine are sufficient to create or permit the initiation and propagation of cracks therein.

Referring now to FIGS. 2 and 3, an expanded view of a portion of the disc member 12 is shown. Experience has indicated that most cracks, such as that indicated by reference numeral 30 in FIG. 2 and shown for illustrative purposes only, occur within the disc 12 in plane 32 that extends longitudinally within the disc 12 through the keyway formed by channels 26 and 28. Thus, it would be desirable to be able to ascertain whether such cracks 30 are being generated within the expected plane of cracking 32 disposed within the disc 12. Since visual inspection of a fabricated disc is impossible, ultrasonic techniques have been used.

To facilitate ultrasonic inspection of a fabricated rotor disc at the turbine field site, this invention disposes on the external surface of the hub 16 a flat surface area 34. The surface area 34 is disposed such that it extends substantially parallel to the predetermined expected plane of fracture 32 located within the disc 12. In order to ultrasonically inspect the disc 12, for the detection of cracks 30 within the expected plane of cracking 32, a transducer element 36 is disposed adjacent the flat external surface area 34. A suitable acoustic couplant 38, such as oil film, is disposed between the transducer 36 and the surface area 34. An ultrasonic signal 40 emitted by the transducer 36 in a beam substantially perpendicular to the expected plane of cracking 32 passes into the material of the disc 12 through the coupling 38. It is well known in the art of non-destructive testing that ultrasonic inspection wherein the interrogating beam impinges upon cracks in a substantially perpendicular direction thereto yields the best result.

The surface area 34 on the hub portion 16 of the disc 12 is machined onto the disc 12 before the disc is heated prior to its being fitted over the shaft 10. Once allowed to cool, an ultrasonic scan may be made in a manner similar to that described above. Such a preliminary ultrasonic inspection will document the ultrasonic response from the unflawed keyway and serve as a reference point for future field tests. Once fabricated, and disposed in a completed turbine, on-site inspection of the disc 12 may be expeditiously and reliably performed.

It is well known in the art that cracking of rotor discs in the expected plane of cracking 32 within the disc 12 itself occurs due to the effects of stresses imposed upon the disc by operation of the turbine. In general, two mechanisms may lead to cracking within the disc 14. Such mechanisms are stress corrosion cracking and fatigue crack growth.

Stress corrosion cracking occurs under the combined influence of static stress and deleterious environment. In general, such cracking is usually intergranular in nature for the metal used to fabricate turbine discs.

Fatigue crack growth occurs under the influence of an alternating stress. Such stress occurs when the turbine goes from rest (0 RPM) to running speed (1800 RPM). The presence of a deleterious environment will generally accelerate (increase the growth per cycle) fatigue crack growth.

In a steam turbine apparatus, the operating environment (steam plus impurities) combined with the stresses caused by rotation and the shrink fit, can in extreme cases cause cracking in the predetermined plane 32 within the rotor disc 12.

Ultrasonic inspection using the external surface area 34 machined onto the hub 16 of the disc 12 will permit on-site inspection of rotor discs expeditiously and reliably. Thus, the development of cracks within the rotor disc can be quickly and accurately ascertained thus preventing catastrophic consequences attendant upon bursting of damaged discs.

We claim as our invention:

1. A rotor for an axial flow turbine apparatus comprising:
    a shaft member,
    a disc member mounted on said shaft member,
    a key disposed between said disc and said shaft, said disc having a flat surface externally thereon capable of operably receiving a detector, said flat surface on said disc being disposed substantially parallel to a predetermined expected plane of fracture within the disc so that an ultrasonic signal emitted from said detector mounted against said flat surface propagates through said disc in a direction substantially perpendicular to said plane which also normally extends longitudinally through said key.

2. The rotor of claim 1, wherein said disc has a hub portion disposed adjacent to a steeple portion, said hub portion having a radially outer dimension that is less than the radially outer dimension of said steeple, said flat surface being disposed on said hub portion.

3. The rotor of claim 1, wherein said flat surface is disposed substantially parallel to said plane through said key.

* * * * *